(12) United States Patent
Hsieh (10) Patent No.: US 6,421,411 B1
(45) Date of Patent: Jul. 16, 2002

(54) METHODS AND APPARATUS FOR HELICAL IMAGE ARTIFACT REDUCTION (75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/853,145

(22) Filed: May 10, 2001

(51) Int. Cl.$^7$ ................................................ A61B 6/00
(52) U.S. Cl. .............................. 378/4; 378/19; 378/901
(58) Field of Search ................ 378/4, 19, 21, 378/901

(56) References Cited

U.S. PATENT DOCUMENTS

| | | |
|---|---|---|
| 5,416,815 A | 5/1995 | Hsieh |
| 5,515,409 A * | 5/1996 | Hsieh .......................... 378/15 |
| 5,610,964 A * | 3/1997 | Flohr et al. .................. 378/15 |
| 5,727,041 A | 3/1998 | Hsieh |
| 5,812,628 A | 9/1998 | Hsieh |
| 6,035,012 A | 3/2000 | Hsieh |
| 6,061,419 A | 5/2000 | Hsieh et al. |
| 6,061,420 A | 5/2000 | Strong et al. |
| 6,233,308 B1 | 5/2000 | Hsieh |
| 6,115,487 A | 9/2000 | Toth et al. |
| 6,134,292 A * | 10/2000 | Hsieh .......................... 378/19 |
| 6,215,841 B1 | 4/2001 | Hsieh |

* cited by examiner

Primary Examiner—David V. Bruce
Assistant Examiner—Pamela R. Hobden
(74) Attorney, Agent, or Firm—Carl B. Horton, Esq.; Armstrong Teasdale LLP (57) ABSTRACT

Methods and apparatus are provided for reducing image artifacts from a computed tomography (CT) image generated using a CT system. A plurality of projection views of an object are obtained and a plane of reconstruction including reconstructed images is defined. A smoothing function is applied to the reconstructed images to reduce image artifacts wherein a greater amount of z-smoothing is applied to images located a greater distance from an iso-center.

42 Claims, 4 Drawing Sheets

METHODS AND APPARATUS FOR HELICAL IMAGE ARTIFACT REDUCTION

BACKGROUND OF THE INVENTION

This invention relates generally to methods and apparatus for CT imaging and other radiation imaging systems and, more particularly, to z-smoothing for helical image artifact reduction.

In at least some "computed tomography" (CT) imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is the filtered back projection technique. This process converts the attenuation measurements from a scan into integers called "CT numbers" or "Hounsfield units," which are used to control the brightness of a corresponding pixel on a cathode ray tube display.

To reduce the total scan time required for multiple slices, a "helical" scan may be performed. To perform a "helical" scan, the patient is moved in a z-axis direction synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three dimensional images.

The x-ray beam is projected from the x-ray source through a pre-patient collimator that defines the x-ray beam profile in the patient axis, or z-axis. The collimator typically includes x-ray-absorbing material with an aperture therein for restricting the x-ray beam. In at least one known CT imaging system, a scanning mode and corresponding reconstruction method are implemented for 3:1 and 6:1 helical pitches. The 6:1 helical pitch mode is referred to as a "high speed" (HS) mode because volume coverage is large, and scanning is faster along z-axis than in the 3:1 helical pitch mode.

In some CT imaging systems, the detector array is segmented so that a plurality of quasi-parallel slices of projection data are acquired and processed to construct a plurality of images corresponding to several slices though a volume. Such CT imaging systems are referred to as "multislice" systems. Multislice systems provide more data available for reconstructing an image.

In one exemplary embodiment of a multislice scanner, N rows, e.g., N slices, of projection data are acquired for each view angle. A range of pitches exists for which measurements are available at least at two source locations. Measurements acquired at different source positions are known as "conjugate measurements." Pitches for which conjugate measurements are available are known as "High Quality" (HQ) pitches. When an HQ pitch is used, a CT imaging system is said to operate in "HQ mode." For a range of pitches for which majorities of measurements are available at only one source position are known as "High Speed" (HS) pitches. When an HS pitch is used, a CT imaging system is said to operate in "HS mode." The availability of multislice data allows interpolation/extrapolation from different rows at the same source position. Higher HS pitches are made possible by allowing data extrapolation. Increasing the number of slices in a multislice imaging system, however, leads to increased cone angles which have a detrimental effect on image quality.

At least one known CT imaging system utilizes a detector array and a "data acquisition system" (DAS) for collecting image data. The detector array includes detector cells or channels that each produce an analog intensity signal representing x-ray energy impinging on the detector cell. The analog signals are then converted by the DAS to digital signals, which are used to produce image data. Detector cell degradation, as measured by gain non-linearity, typically produces ring or band annoyance artifacts.

BRIEF SUMMARY OF THE INVENTION

Methods and apparatus are provided for reducing image artifacts from a computed tomography (CT) image generated using a CT system. In one aspect a method for reconstructing a computed tomography image of an object is provided which comprises scanning an object utilizing a step-and-shoot mode to acquire a plurality of projection views of the object, reconstructing an image based on projection data from a particular detector row, determining a smoothing function based on a cone angle of the detector row and an image pixel distance from an iso-center, and applying the smoothing function to the reconstructed image.

In another aspect, a method is provided for reconstructing a computed tomography image of an object which comprises scanning an object utilizing helical mode to acquire a plurality of projection views of the object, reconstructing an image based on projection data from a plurality of detector rows, determining a z-smoothing function based on at least one of a helical pitch, an image pixel distance from an iso-center, a number of detector rows, a reconstruction algorithm, and a slice thickness for the particular detector row, and applying the z-smoothing function to the reconstructed image and applying the z-smoothing function to pixels within the reconstructed image, the amount of smoothing applied to an individual of image pixel in the reconstructed image based on a location of the pixel from the iso-center.

In still another aspect, an imaging system is provided which comprises a computer, a gantry having a detector array, an x-ray source for radiating an x-ray beam along an imaging plane toward a detector array including a plurality of detector cells, the computer coupled to the x-ray source and the gantry, where the imaging system is configured to scan an object utilizing step-and-shoot mode to acquire a plurality of projection views of the object, reconstruct an image based on projection data from a particular detector row, determine a smoothing function based on a cone angle of each detector row and an image pixel distance from an iso-center, and apply the smoothing function to the reconstructed image.

In yet another aspect, an imaging system is provided which comprises a computer, a gantry having a detector array, an x-ray source for radiating an x-ray beam along an imaging plane toward a detector array including a plurality of detector cells arranged in rows, the computer coupled to the x-ray source and the gantry, where the imaging system is configured to scan an object utilizing helical mode to acquire a plurality of projection views of the object, reconstruct an image based on acquired projection data, determine a z-smoothing function based on at least one of a helical pitch, an image pixel distance from an iso-center, a number of detector rows, a reconstruction algorithm, and a slice thickness for each particular detector row, and apply the z-smoothing function to pixels within the reconstructed image, the amount of smoothing applied to an individual of image pixel in the reconstructed image based on a location of the pixel from the iso-center.

In another aspect a processor is provided which is programmed to reduce image artifacts in a computed tomography system. The processor is configured to scan an object to acquire a plurality of projection views of an object, define a measurement plane, define a plane of reconstruction perpendicular to a patient axis that intersects the measurement plane at an iso-center, reconstruct an image from the plurality of projection views, determine an image pixel distance to the iso-center and a cone angle of detector rows, and apply a z-smoothing weights, based upon the image pixel distance from the iso-center, to at least one detector channel in a z-axis direction to reduce image artifact.

In yet another aspect, a computer-readable medium in an imaging system is provided which comprises a function to acquire projection data for a plurality of detector rows, a function to reconstruct images from the projection data, a function to determine a cone angle for each detector row and an image pixel distance to an iso-center, and a function for applying a z-smoothing function, based upon the image pixel distance from the iso-center, to the reconstructed images to reduce image artifact.

DETAILED DESCRIPTION OF THE INVENTION

Figure 1:
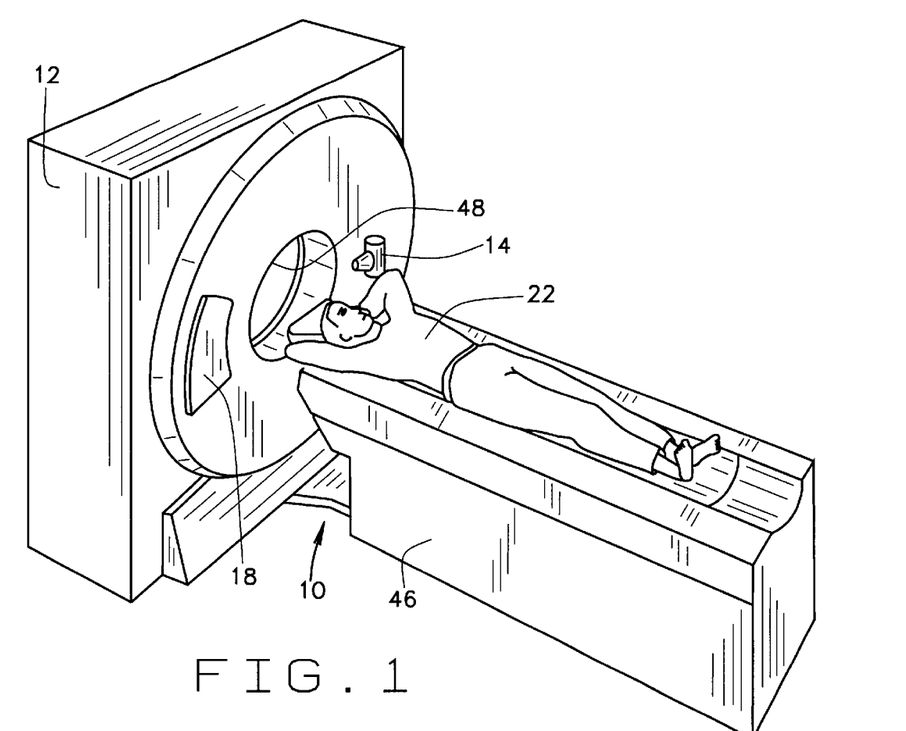
FIG. 1 is a pictorial view of a CT imaging system.
Figure 2:
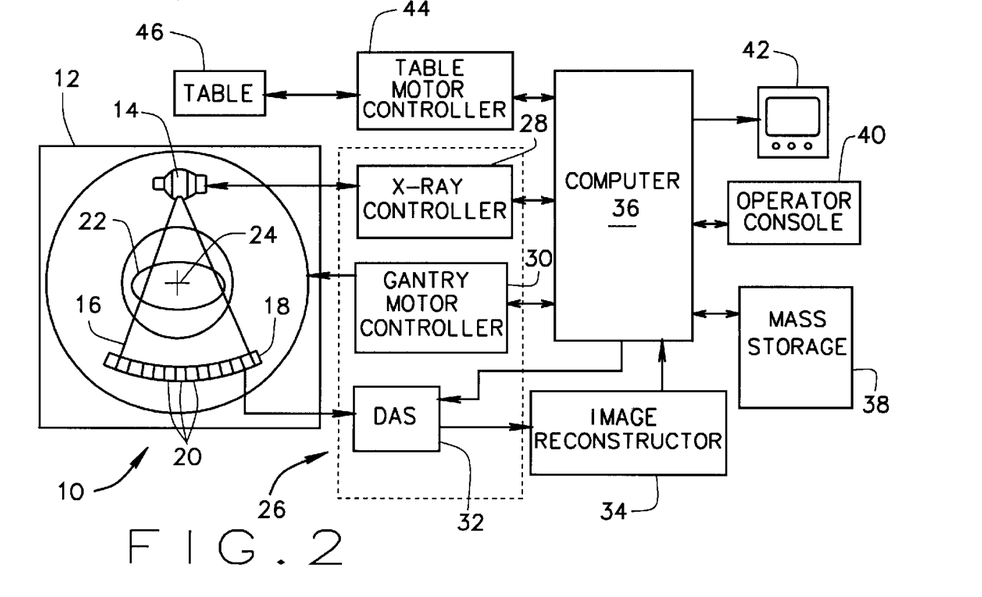
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

It is known that cone beam artifacts present significant problems for the HS mode, i.e., 6:1 pitch, multi-slice helical scans. A known method to reduce image artifacts is the application of z-smoothing. Z-smoothing reduces helical artifacts and x-ray tube current. In discrete form, and in one embodiment, a known z-smoothing equation, including weights $W_{zs}(\beta,\gamma)$, is written as:

$$W_{zs}(\beta, \gamma) = \sum_{i=1}^{T} h(i) \times W(\beta - i \times \Delta\beta, \gamma), \quad (1)$$

where h represents a z-smoothing kernel, T is the number of terms in the z-smoothing kernel, $\Delta\beta$ is the view increment between each image plane contributing through z-smoothing to the final reconstructed image, and W( ) is an unsmoothed weight. Unfortunately, z-smoothing significantly degrades "slice sensitivity profile" (SSP). SSP represents the width of an image slice.

Figure 3:
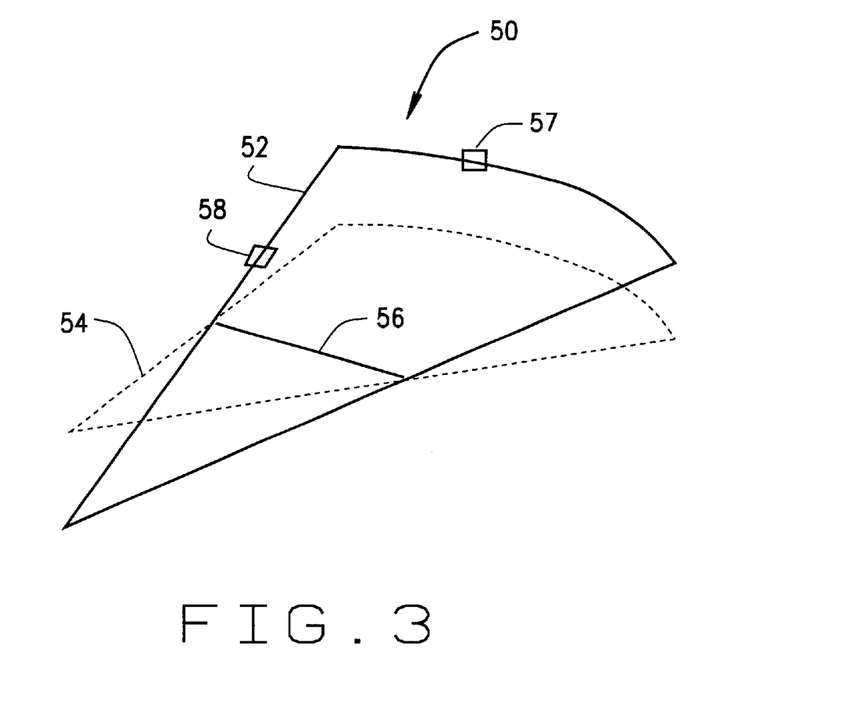
FIG. 3 is an illustration of a projection measurement plane and a reconstruction plane.

FIG. 3 is an illustration 50 of a projection measurement plane 52 and a plane of reconstruction 54. Projection measurement plane 52 includes projection measurement samples obtained during a scan of object 22 (shown in FIG. 1). Reconstruction plane 54 is a plane that intersects iso-center 56 and is perpendicular to a patient axis. Projection measurement plane 52 and reconstruction plane 54 overlap at iso-center 56. The geometric distance between the two planes increases with the increase of distance from iso-center 56. Projection sampling is quite accurate at iso-center 56 because measurement plane 52 and reconstruction plane 54 overlap, however, for samples located away from iso-center 56, a cone beam effect causes the accuracy to degrade. In one embodiment, reconstruction plane 54 lays in a horizontal plane and measurement plane 52 lays in a plane obliquely offset by a cone angle with respect to reconstruction plane 54. The cone angle of measurement plane 52 increases the further a measurement sample, e.g., an image pixel, is located away from iso-center 56. A smoothing function is applied to measurement plane 52. No smoothing is applied to samples located at iso-center 56. The amount of z-smoothing applied to the measurement sample depends on the distance the sample is located from iso-center 56. For example, in one embodiment, a proportionally greater amount of z-smoothing is applied to measurement sample 57 compared to measurement sample 58. For instance, at iso-center 56, the SSP is identical to an original reconstructed image and as the distance of a reconstructed image increases from iso-center 56, the SSP increases.

Figure 4:
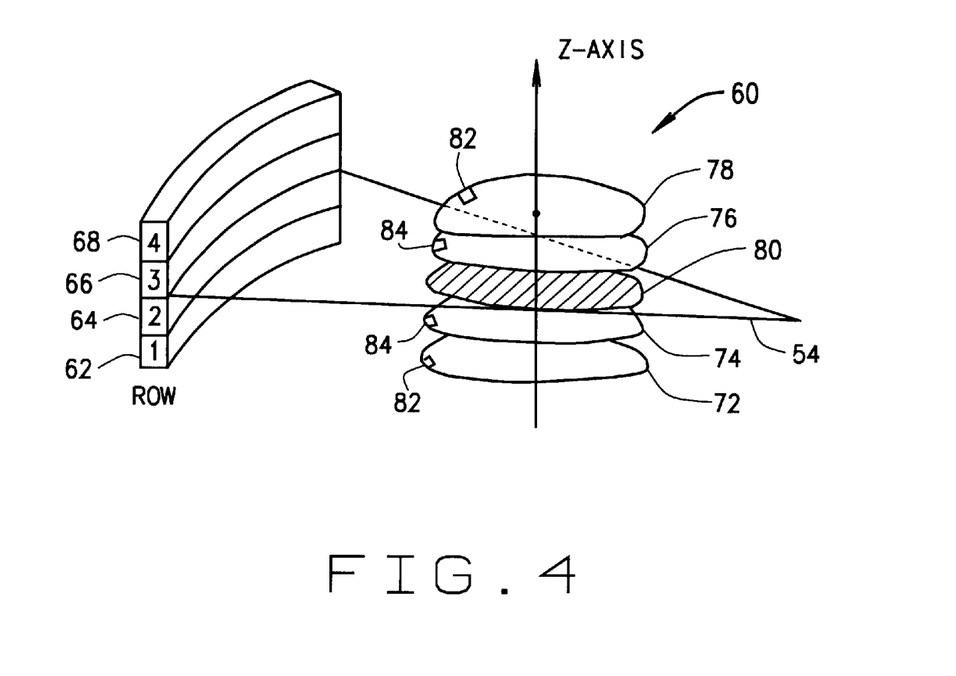
FIG. 4 is a diagram illustrating images generated from adjacent detector rows.

FIG. 4 is a diagram 60 illustrating images generated from adjacent detector rows with respect to reconstruction plane 54 (shown in FIG. 3). Using four detector rows 62, 64, 66, and 68, four images 72, 74, 76, and 78 are generated, the images generated each being associated with a measurement plane 52 (shown in FIG. 3) which intersects reconstruction plane 54. Measurement samples used to generate images 72, 74, 76, and 78 are located a distance from a center plane 80 and therefore are also located at an angle, the cone angle, from center plane 80, which has a cone angle of 0 degrees. The amount of z-smoothing applied to each sample within images 72, 74, 76, and 78 depends on the distance the sample is located from center plane 80. As shown in the Figure, a greater cone angle effect exists for samples 82 within images 72 and 78 and therefore need more z-smoothing than do samples 84 within images 74 and 76, based upon a cone angle from reconstruction plane 54, that is, distance from iso-center 56. In addition, within each image, for example, image 74, the amount of z-smoothing is minimum for pixels located near iso-center 56 and the amount of z-smoothing is greatest for pixels at an edge of a field of view. For example, pixel 84 has a maximum amount of z-smoothing applied compared to other pixels (not shown) in image 74.

Figure 5:
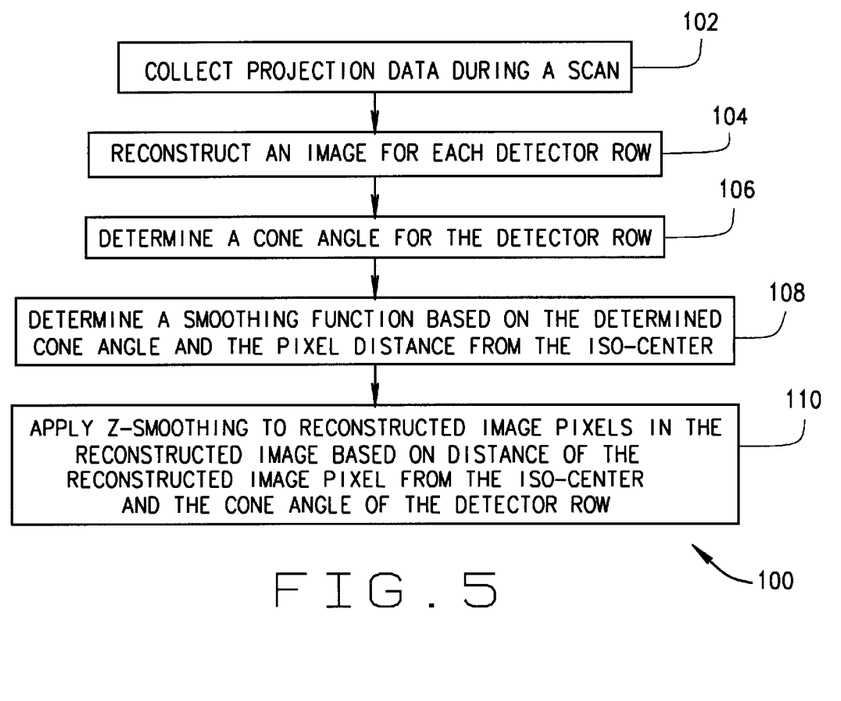
FIG. 5 is a flow chart illustrating the steps executed by the CT system in step-and-shoot mode to reduce image artifacts by applying a smoothing function.

FIG. 5 is a flow chart 100 illustrating the steps CT imaging system 10, operating in step-and-shoot mode, performs when applying a smoothing function to minimize image artifacts. The method illustrated in FIG. 4 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

Referring specifically to FIG. 5, a set of raw scan data is acquired in a step-and-shoot-mode with patient table 46 (shown in FIG. 1) stationary. The raw scan data is pre-processed to generate 102 a set of projection data. The projection data is used to reconstruct 104 an image for each fixed detector row, e.g., an image will be reconstructed from data from each detector row. A cone angle is determined 106 for the detector row. Detector rows located away from the detector center plane (a plane with a cone angle of 0 degrees), include a greater amount of image artifact because of the oblique angle of a measurement plane, such as measurement plane 52 (shown in FIG. 3) compared to a reconstruction plane, such as reconstruction plane 54 (shown in FIG. 3). A smoothing function is determined 108 based on the cone angle determination 106 and the pixel distance from iso-center 56. In one embodiment, detector rows near the center plane are referred to as "inner detector rows" and detector rows located farthest away from the center plane are referred to as "outer detector rows." The z-smoothing function is applied 110 to the reconstructed image. The amount of z-smoothing applied 110 to image pixels in the reconstructed image is proportional to the distance of the reconstructed image pixel from iso-center 56. In addition, the amount of z-smoothing applied to the reconstructed image pixel is proportional to the cone angle of the detector row. In one embodiment, less z-smoothing is applied to image pixels generated by inner detector rows because of the smaller cone angle of the "inner detector rows." An increased amount of z-smoothing is applied 110 to image pixels generated by detector rows located farthest from the center plane because of the larger cone angle of the "outer detector rows."

Figure 6:
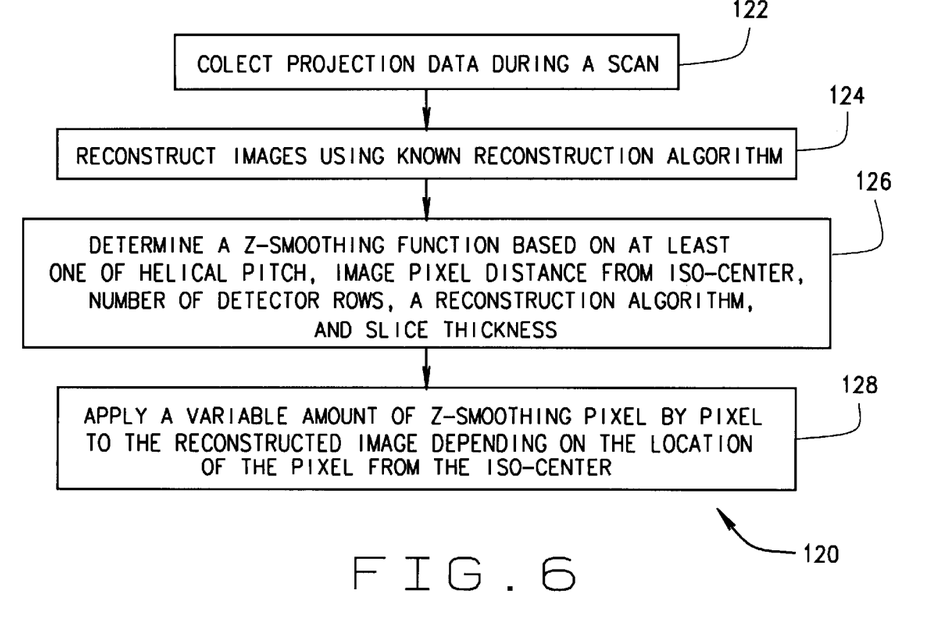
FIG. 6 is a flow chart illustrating the steps executed by the CT system in helical mode to reduce image artifacts by applying a smoothing function.

FIG. 6 is a flow chart 120 illustrating the steps CT imaging system 10, operating in helical mode, performs when applying a smoothing function to minimize image artifacts. The method illustrated in FIG. 6 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

Referring specifically to FIG. 6, a set of raw scan data is acquired and is pre-processed to generate 122 a set of projection data. The projection data is used to reconstruct 124 an image using a known reconstruction algorithm utilizing a helical pitch and slice thickness. In one embodiment, a plurality of images are reconstructed for each detector row, wherein each reconstructed image includes contributions from all detector rows. A z-smoothing function is determined 126 based on at least one of a helical pitch, a number of detector rows, a reconstruction algorithm, and a slice thickness. The z-smoothing function is then applied 128 to each reconstructed image. A variable amount of z-smoothing is applied pixel by pixel to each reconstructed image depending on the location of the pixel from the iso-center, such as iso-center 56 (shown in FIG. 3).

Figure 7:
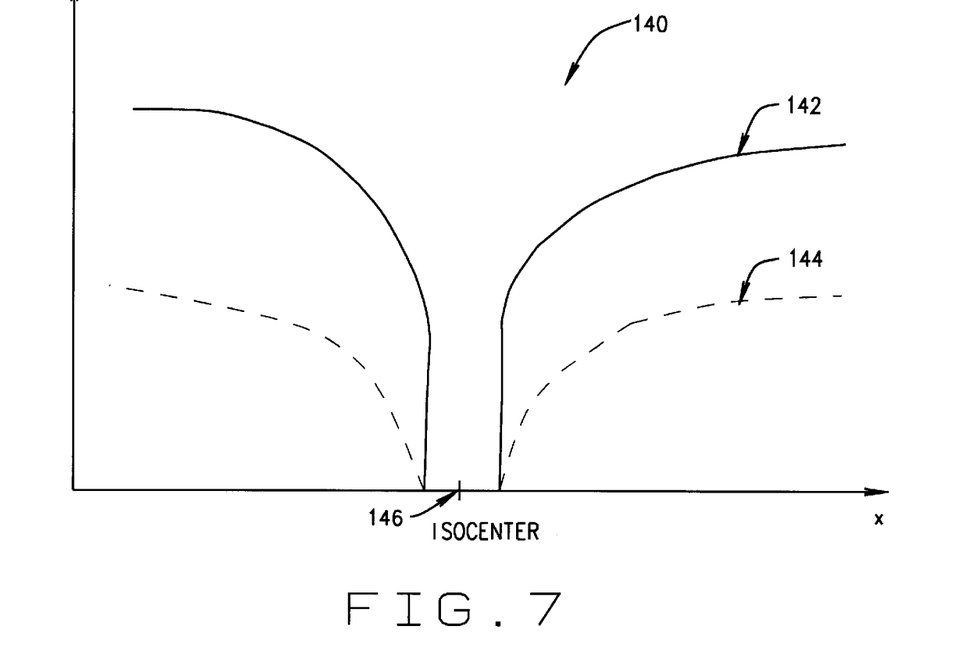
FIG. 7 is a graph representing an amount of z-smoothing applied to various detector rows.

FIG. 7 is a graph 140 representing an amount of z-smoothing applied to various detector rows and the amount of z-smoothing applied to image pixels in a reconstructed image, in either of a step-and-shoot mode or an axial scan mode. In one embodiment, the reconstructed image includes a 512×512 pixel array. Curve 142 represents an amount of z-smoothing applied to an outer row of detectors. Curve 144 represents an amount of z-smoothing applied to an inner row of detectors. Graph 140 shows no z-smoothing is applied at iso-center 146. The farther a detector row is from the center plane, the more z-smoothing is applied. For instance, more z-smoothing is applied to curve 142 compared to curve 144. In addition, graph 140 shows for each reconstructed image the farther an image pixel is from isocenter 146, the greater the amount of z-smoothing is applied. Therefore, the application of z-smoothing is dependent on the location of the detector row from the center plane and the location of the image pixel from the iso-center 146.

Figure 8:
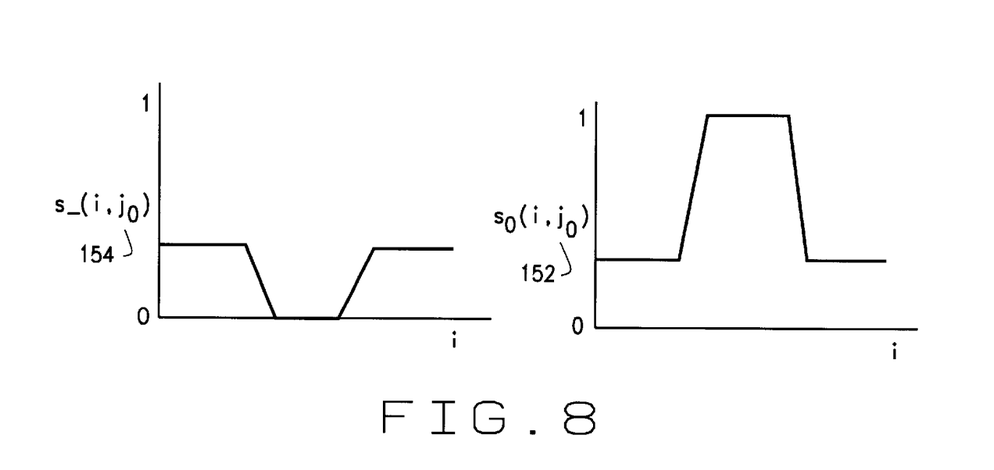
FIG. 8 is an illustration of a z-smoothing weighting function.

FIG. 8 is an illustration 150 of an exemplary embodiment of a z-smoothing weighting function. In one embodiment, a center image, $p_0(i,j)$ (not shown), and two images, $p_-(i,j)$ (not shown) and $p_+(i,j)$ (not shown), are located on either side of $p_0(i,j)$. All these images are located adjacent to a reconstructed image in a z-plane. The two images, $p_-(i,j)$ and $p_+(i,j)$, are used for the z-smoothing operation. Corresponding weighting functions for the three images $p_-(i,j)$, $p_0(i,j)$, and $p_+(i,j)$ are denoted by $s_-(i,j)$ 104, $s_0(i,j)$ 152, and $s_+(i,j)$ 154. In this embodiment, weighting function $s_-(i,j)$ equals $s_+(i,j)$. A resulting image $p(i,j)$ is obtained by the following equation:

$$p(i,j) = s_-(i,j)p_-(i,j) + s_0(i,j)p_0(i,j) + s_+(i,j)p_+(i,j), \quad (2)$$

where $$s_-(i,j) = s_+(i,j) = \begin{cases} 0, & r < r_0 \\ \dfrac{r - r_0}{3(r_1 - r_0)}, & r_0 \leq r < r_1 \\ 1/3, & r \geq r_1, \end{cases}$$

$$s_0(i,j) = 1 - s_-(i,j) - s_+(i,j),$$

where $r = \sqrt{(i-i_0)^2 + (j-j_0)^2}$, and $i_0$ and $j_0$ are the iso-center locations in the image, and the center line profile occurs with $j = j_0$.

The above example illustrates one embodiment of z-smoothing. Many different smoothing functions can be utilized. For example, the number of images used for smoothing, the spacing between the images, and the weighting functions can be dynamically changed based on the helical pitch and the detector configuration. Furthermore, additional z-smoothing is required for higher helical pitches. Similarly, the greater number of slices, the thicker each slice width, and the more acute a cone angle, the greater the amount of z-smoothing required.

In one embodiment, to further reduce the impact of the smoothing on spatial resolution of the image, a threshold for the filtering operation is established. The filtering operation is applied only when a CT number difference between adjacent slices falls below the predefined threshold. As a result, sharp transition regions, e.g., between bone and soft tissue; and between soft tissue and an air pocket, are preserved. In another embodiment, to ensure a smooth transition between the filtered and non-filtered regions, an image mask is generated and the mask is smoothed.

In another embodiment, CT system 10 includes a computer program residing on a computer-readable medium within mass storage 38 for reconstructing the image. A plurality of records of projection data for a plurality of projection views are used to define a measurement plane. To reconstruct an image, a plurality of rules define a plane of reconstruction that intersects the measurement plane at an iso-center, a plurality of rules determine the distance a detector row is from the iso-center, and a plurality of rules apply a z-smoothing weighting function to the records of measurement plane projection data to reduce image artifact.

While the invention has been described in terms of various specific embodiments, those skilled in the art will recognize that the invention can be practiced with modification within the spirit and scope of the claims.

What is claimed is:

1. A method for reconstructing a computed tomography image of an object comprising the steps of:
    scanning an object utilizing step-and-shoot mode to acquire a plurality of projection views of the object;
    reconstructing an image based on projection data from a particular detector row;
    determining a smoothing function based on a cone angle of the detector row and an image pixel distance from an iso-center; and
    applying the smoothing function to the reconstructed image.

2. A method in accordance with claim 1 wherein the reconstructed image comprises a 512×512 pixel array.

3. A method in accordance with claim 1 wherein said step of determining a smoothing function further comprises the step of generating a z-smoothing function.

4. A method in accordance with claim 1 wherein said step of determining a smoothing function further comprises the step of determining at least one of a distance the detector row is located from a center plane and a cone angle for the detector row.

5. A method in accordance with claim 4 wherein said step of generating a z-smoothing function comprises the step of generating z-smoothing weights which increase as distance of the image pixel from the iso-center increases.

6. A method in accordance with claim 5 wherein the z-smoothing weights comprise the following relationship:

$$s_-(i,j) = s_+(i,j) = \begin{cases} 0, & r < r_0 \\ \dfrac{r - r_0}{3(r_1 - r_0)}, & r_0 \leq r < r_1 \\ 1/3, & r \geq r_1, \end{cases}$$

$$s_0(i,j) = 1 - s_-(i,j) - s_+(i,j),$$

where $r = \sqrt{(i-i_0)^2 + (j-j_0)^2}$, and $i_0$ and $j_0$ are iso-center locations in an image.

7. A method in accordance with claim 3 wherein said step of applying a smoothing function to the reconstructed image further comprises the step of applying a z-smoothing function to a plurality of pixels in the reconstructed image.

8. A method in accordance with claim 7 wherein said step of applying a z-smoothing function to a plurality of pixels further comprises the step of applying an increased amount of smoothing to image pixels located farther away from an iso-center.

9. A method for reconstructing a computed tomography image of an object comprising the steps of:
    scanning an object utilizing helical mode to acquire a plurality of projection views of the object;
    reconstructing an image based on projection data from a plurality of detector rows;
    determining a z-smoothing function based on at least one of a helical pitch, an image pixel distance from an iso-center, a number of detector rows, a reconstruction algorithm, and a slice thickness for the particular detector row; and applying the z-smoothing function to the pixels within the reconstructed image, the amount of smoothing applied to an individual image pixel in the reconstructed image based on a location of the pixel from the iso-center.

10. A method in accordance with claim 7 wherein the reconstructed image comprises a 512×512 pixel array.

11. A method in accordance with claim 9 wherein said step of determining a z-smoothing function further comprises the step of determining a distance the particular detector row is located from a center plane.

12. A method in accordance with claim 9 wherein said step of applying the z-smoothing function comprises the step of determining a location of an image pixel within a reconstructed image.

13. A method in accordance with claim 12 wherein said step of determining a location of an image pixel further comprises determining a distance from the image pixel to the iso-center.

14. A method in accordance with claim 13 wherein said step of applying a smoothing function further comprises the step of applying an increased amount of smoothing to image pixels located farther away from the iso-center.

15. An imaging system comprising a computer, a gantry having a detector array, an x-ray source for radiating an x-ray beam along an imaging plane toward a detector array including a plurality of detector cells, the computer coupled to the x-ray source and the gantry, said imaging system configured to:
   scan an object utilizing step-and-shoot mode to acquire a plurality of projection views of the object;
   reconstruct an image based on projection data from a particular detector row;
   determine a smoothing function based on a cone angle of each detector row and an image pixel distance from an iso-center; and
   apply the smoothing function to the reconstructed image.

16. An imaging system in accordance with claim 15 wherein said reconstructed image comprises a 512×512 pixel array.

17. An imaging system in accordance with claim 15 wherein said imaging system is configured to determine a distance the detector row is located from a center plane and a cone angle for the detector row.

18. An imaging system in accordance with claim 15 wherein said smoothing function comprises a z-smoothing function.

19. An imaging system in accordance with claim 18 wherein said z-smoothing function comprises z-smoothing weights.

20. An imaging system in accordance with claim 19 wherein said z-smoothing weights comprise the following relationship:

$$s_-(i,j) = s_+(i,j) = \begin{cases} 0, & r < r_0 \\ \dfrac{r - r_0}{3(r_1 - r_0)}, & r_0 \le r < r_1 \\ 1/3, & r \ge r_1, \end{cases}$$

$$s_0(i,j) = 1 - s_-(i,j) - s_+(i,j),$$

where $r = \sqrt{(i-i_0)^2 + (j-j_0)^2}$, and $i_0$ and $j_0$ are iso-center locations in an image.

21. An imaging system in accordance with claim 15 wherein said imaging system is configured to apply a z-smoothing function to a plurality of pixels in the reconstructed image.

22. An imaging system in accordance with claim 21 wherein said imaging system is configured to apply an increased amount of smoothing to image pixels located farther away from an iso-center.

23. An imaging system in accordance with claim 15 wherein said imaging system is configured to apply an amount of z-smoothing proportional to a distance the detector row is from a center plane and a cone angle for the detector row.

24. An imaging system in accordance with claim 23 wherein said imaging system is configured to apply more z-smoothing to a detector row based on the distance the detector row is from the iso-center.

25. An imaging system in accordance with claim 15 wherein said imaging system is configured to apply no z-smoothing at the iso-center.

26. An imaging system in accordance with claim 15 wherein said imaging system is configured to apply z-smoothing in a z-axis direction.

27. An imaging system comprising a computer, a gantry having a detector array, an x-ray source for radiating an x-ray beam along an imaging plane toward a detector array including a plurality of detector cells arranged in rows, the computer coupled to the x-ray source and the gantry, said imaging system configured to:
   scan an object utilizing helical mode to acquire a plurality of projection views of the object;
   reconstruct an image based on acquired projection data;
   determine a z-smoothing function based on at least one of a helical pitch, an image pixel distance from an iso-center, a number of detector rows, a reconstruction algorithm, and a slice thickness for each particular detector row; and
   apply said z-smoothing function to pixels within the reconstructed image, the amount of smoothing applied to an individual image pixel in the reconstructed image based on a location of the pixel from the iso-center.

28. An imaging system in accordance with claim 27 wherein the reconstructed image comprises a 512×512 pixel array.

29. An imaging system in accordance with claim 27 wherein said step of determining a z-smoothing function further comprises the step of determining a distance for each particular detector row from a center plane.

30. An imaging system in accordance with claim 27 wherein said imaging system is configured to determine a location of an image pixel within a reconstructed image.

31. An imaging system in accordance with claim 30 wherein said imaging system is configured to determine a distance from the image pixel to the iso-center.

32. An imaging system in accordance with claim 31 wherein said imaging system is configured to apply an increased amount of z-smoothing to image pixels located farther away from the iso-center.

33. An imaging system in accordance with claim 27 wherein said imaging system is configured to apply no z-smoothing at the iso-center.

34. A processor programmed to reduce image artifacts in a computed tomography system, said processor configured to:
   scan an object to acquire a plurality of projection views of an object;
   define a measurement plane;
   define a plane of reconstruction perpendicular to a patient axis that intersects the measurement plane at an iso-center;

reconstruct an image from the plurality of projection views;

determine an image pixel distance to the iso-center and a cone angle of detector rows; and apply a z-smoothing weights, based upon the image pixel distance from the iso-center, to at least one detector channel in a z-axis direction to reduce image artifact.

35. A processor in accordance with claim 34 wherein said measurement plane is parallel to said plane of reconstruction.

36. A processor in accordance with claim 34 further configured to apply an amount of z-smoothing proportional to a distance of image pixels from the iso-center.

37. A processor in accordance with claim 36 further configured to apply a larger amount of z-smoothing as a distance of image pixels from the iso-center increases.

38. A computer-readable medium in an imaging system, said computer-readable medium comprising:

a function to acquire projection data for a plurality of detector rows;

a function to reconstruct images from the projection data;

a function to determine a cone angle for each detector row and an image pixel distance to an iso-center; and a function for applying a z-smoothing function, based upon the image pixel distance from the iso-center, to the reconstructed images to reduce image artifact.

39. A computer-readable medium in accordance with claim 38 wherein images are reconstructed from projection data corresponding to a particular detector row.

40. A computer-readable medium in accordance with claim 38 wherein the images are reconstructed from projection data corresponding to a plurality of detector rows.

41. A computer-readable medium in accordance with claim 38 wherein the amount of z-smoothing applied to the reconstructed images is in proportion to the distance the corresponding detector row is from a center plane and the cone angle for the detector row.

42. A computer-readable medium in accordance with claim 41 wherein the amount of z-smoothing is increased as image pixel distance from the iso-center increases.

* * * * *

UNITED STATES PATENT AND TRADEMARK OFFICE
CERTIFICATE OF CORRECTION

PATENT NO.     : 6,421,411 B1  
DATED          : July 16, 2002  
INVENTOR(S)    : Hsieh It is certified that error appears in the above-identified patent and that said Letters Patent is hereby corrected as shown below:

Column 11,  
Line 5, delete "a".

Signed and Sealed this

Twenty-sixth Day of August, 2003

JAMES E. ROGAN  
*Director of the United States Patent and Trademark Office*